United States Patent [19]

Pasquale

[11] Patent Number: 4,530,839
[45] Date of Patent: Jul. 23, 1985

[54] TRIPHASIC ORAL CONTRACEPTIVE

[75] Inventor: Samuel A. Pasquale, Basking Ridge, N.J.

[73] Assignee: Ortho Pharmaceutical Corporation, Raritan, N.J.

[21] Appl. No.: 536,135

[22] Filed: Sep. 26, 1983

[51] Int. Cl.³ .............................................. A01N 45/00
[52] U.S. Cl. ..................................... 514/171; 514/843
[58] Field of Search ........................ 424/238, 241, 239

[56] References Cited

U.S. PATENT DOCUMENTS 4,291,028  9/1981  Vorys .................................. 424/238
4,378,356  3/1983  De Jager ............................ 424/238

Primary Examiner—Elbert L. Roberts
Attorney, Agent, or Firm—Benjamin F. Lambert

[57] ABSTRACT

A method of contraception in which an estrogen and a progestogen are administered daily for 21 days, the first seven days at a low contraceptively effective daily dose, the next 7 days at a daily progestogen dose about 1.5–2 times that of the first 7 days, and the next 7 days at a daily progestogen dose of 2–2.5 times that of the first 7 days, provided that the dosage of the estrogen is maintained at a constant level for the entire 21 days.

9 Claims, No Drawings

TRIPHASIC ORAL CONTRACEPTIVE

This invention relates to a method of contraception comprising the oral administration of a low but contraceptively effective daily dosage of an estrogen and a progestogen for 21 successive days.

Oral contraceptives first became available in the early 1960's. Through continued research, new lower-dose estrogen products of high effectiveness have been developed. The oral administration of combination type preparations containing estrogens and progestogens has been known for some time. The administration of purely sequential preparations wherein an estrogen is administered at a high dosage in the absence of a gestagen, over a period of 7 days, and thereafter the estrogen is administered at the same high dosage in combination with a relatively high amount of a progestogen over a period of 15 days, with the next 6 days being a blank period without administration of estrogen or progestogen in order to mimic the normal 28-day menstrual cycle of the woman, is also known.

Two stage or bi-phasic combination type oral contraceptives, wherein a combination of an estrogen at a low dosage and a progestogen at a low dosage first being administered for 10-12 days and subsequently a combination of the same dosage of estrogen and a dosage of progestogen increased to 2-3 times as much is administered for 11-9 days, were developed in an effort to reduce dosage and keep bleeding patterns at an acceptable level. This sequence is generally followed by a 5-7 day hormone-free period during which no estrogen or progestogen is ingested in an effort to adapt to the normal 28-day female cycle.

One disadvantage inherent in the administration of the aforementioned pure and modified sequential products involving the administration of relatively high doses of estrogen, in addition to the usual symptoms due to excessive estrogen, i.e., gastrointestinal disturbances, nausea, weight gain with formation of edema, etc., is an increase in the risk of thromboembolic disease. Many of these disadvantages can be avoided by the administration of the above-described two-stage combination contraceptives, but even in the two-stage products it would be desirable if the compatibility and/or the control of the cycle could be improved.

It is also known to administer three-stage combination type oral contraceptives wherein a low contraceptively effective daily dose of an estrogen and a progestogen are administered for the first 4-6 days, and for the next 4-6 days a daily estrogen dose 1-2 times and a daily progestogen dose 1-1.5 times that of the first 4-6 days and for the next 9-11 days at a daily estrogen dose from that of the first 4-6 days to that of the next 4-6 days and a daily progestogen dose higher than either prior daily dose, up to 3 times that of the initial dose. (See U.S. Pat. No. 3,957,982). In this regimen, however, the dosage of both the estrogen and the progestogen is varied during the 21-day cycle.

In recent years data collected on the use of various oral contraceptive regimens have indicated that increased blood pressure and decreased glucose tolerance are associated with the progestogen content or progestational activity of oral contraceptives. In addition, the progestogen activity is associated with a decrease in serum high density lipoprotein values. These findings have prompted a greater emphasis on a reduction of the progestogen dosage in oral contraceptives.

There is a need, therefore, for a combination type contraceptive which contains low concentrations of estrogen and progestogen but is still effective for the prevention of pregnancy.

By the present invention a triphasic oral contraceptive regimen is provided wherein the estrogen dosage is kept constant throughout the 21-day cycle while the progestogen dosage is gradually increased in succesive doses. The purpose of the invention is to lower total monthly steroid dose in the oral contraceptive while still obtaining equivalent bleeding patterns and protection against pregnancy as found with conventional oral contraceptives.

According to the present invention, reliable contraception is achieved by administering for 21 successive days to a female a combination of an estrogen and a progestogen, for the first 7 days in a contraceptively effective daily dosage of about 0.125-0.75 mg of a progestogen in combination with about 0.02-0.05 mg of an estrogen; for the next 7 days, in a daily dosage of about 0.50-1.0 mg of a progestogen together with about 0.02-0.50 mg of an estrogen; and for the last 7 days a daily dosage of about 0.75-2.0 mg of a progestogen in combination with about 0.02-0.05 mg of an estrogen, provided that the dosage of estrogen is kept constant in each phase during the 21-day cycle. The actual weight amount of the dosage at each dosage level will depend upon the estrogenic and progestogenic activity, respectively, of the components selected for the dosage units.

The total number of days during which the progestogen and estrogen combinations are administered daily is 21. These are followed by 7 days which are free of hormone administration to approximate the natural 28-day menstrual cycle of the female. In actual practice a placebo or any other hormone-free agent such as, for example, iron supplements, may be administered during this period.

The contraceptive composition employed in the present invention comprises 21 separate daily dosage units which are adapted for successive daily oral ingestion. In a preferred embodiment, the composition consists essentially of, as the first phase, 7 dosage units containing, in admixture with a pharmaceutically acceptable carrier, a combination of about 0.035 mg of an estrogen in combination with 0.5 mg of progestogen, followed by, as the second phase, 7 dosage units containing, in admixture with a pharmaceutically acceptable carrier, a combination of 0.035 mg of an estrogen and 0.75 mg of a progestogen, followed by, as the third phase, 7 dosage units containing in admixture with a pharmaceutically acceptable carrier a combination of 0.035 mg of an estrogen and 1.0 mg of a progestogen.

Any conventional estrogen may be employed as a suitable component in the contraceptive regimen of this invention. The particular regimen employed in a daily dosage should be equal in contraceptive activity in each phase to a daily dosage of about 0.020-0.050 mg of 17α-ethinylestradiol. The preferred dosage is one equal to a daily dosage of about 0.035 mg of 17α-ethinylestradiol.

In addition to 17α-ethinylestradiol, esters and ethers of 17α-ethinylestradiol may also be employed as the estrogen component. Natural estrogens such as estrone, estradiol and estriol, and their esters, as well as the synthetic estrogens, may also be employed. The preferred estrogen is 17α-ethinylestradiol.

As the progestogen component, any progestationally active compound may be employed. The progestogen is preferably administered in a daily dosage in the first 7 days corresponding in progestogenic activity to 0.125–0.75 mg of norethindrone per day, during the next 7 days a daily dosage corresponding in progestogenic activity to 0.50–1.0 mg of norethindrone per day and during the last 7 days a daily dosage corresponding in progestogenic activity to 0.75–2.0 mg of norethindrone per day.

Progestogens which may be employed as a component in the present invention include progesterone and its derivatives such as, for example, 17-hydroxyprogesterone esters and 19-nor-17-hydroxyprogesterone esters, 17α-ethinyltestosterone, 17α-ethinyl-19-nortestosterone and derivatives thereof, norethindrone, and D-17β-acetoxy-13β-ethyl-17α-ethinyl-gon-4-en-3-one oxime. The preferred progestogens are norethindrone, d-norgestrel and D-17β-acetoxy-13β-ethyl-17α-ethinyl-gon-4-en-3-one oxime.

The estrogen and progestogen components are preferably administered together orally, but they can also be administered separately or parenterally. In general, the effective agents are processed, together with the usual additives, vehicles and/or flavor-ameliorating agents normally employed in Galenic pharmacy, in accordance with generally accepted pharmaceutical practices. For the preferred oral administration, tablets, dragees, capsules, pills, suspensions or solutions are particularly suitable; for parenteral application, oily solutions such as, for example, sesame oil or castor oil solutions which can optionally additionally contain a diluent such as, for example, benzyl benzoate or benzyl alcohol.

In the case of the preferred oral application, the three-phase combination-type contraceptives are preferably packaged in the form of a pharmaceutical kit or package in which the daily dosages are arranged for proper sequential administration. This invention also relates, therefore, to pharmaceutical packages which contain combination-type contraceptives in 28 dosage units in a synchronized, fixed sequence, wherein the sequence or arrangement of the dosage units corresponds to the stages of daily administration.

The pharmaceutical package can be, e.g., in the form of a transparent package having 28 dosage units arranged sequentially and consisting of 7 tablets for the first phase, followed by 7 tablets for the second phase, followed by 7 tablets for the third phase, and finally followed by 7 placebos. A single tablet is to be taken each day over a period of 28 days.

Without further elaboration it is believed that one skilled in the art, using the preceding description, can fully utilize the present invention. The following preferred specific embodiments are to be construed as merely illustrative of the invention and are not meant to limit the invention in any way.

EXAMPLE 1

Composition of a tablet for each stage:

1st Stage 7 Tablets
0.036 mg. 17α-ethinylestradiol
0.50 mg. norethindrone
88.9 mg. lactose anhydrous DT
10.0 mg. pregalatanized starch N.F.
0.5 mg. magnesium stearate N.T.
99.936 mg. total weight 2nd Stage 7 Tablets
0.036 mg. 17α-ethinylestradiol
0.75 mg. norethindrone
88.70 mg. lactose anhydrous DT
10.02 mg. pregalatanized starch N.F.
0.5 mg. magnesium stearate N.T.
100.06 mg. total weight 3rd Stage 7 Tablets
0.036 mg. 17α-ethinylestradiol
1.0 mg. norethindrone
88.5 mg. lactose anhydrous DT
10.0 mg. pregalatanized starch N.F.
0.5 mg. magnesium stearate N.T.
100.036 mg. total weight

EXAMPLE 2

Composition of a tablet for each stage:

1st Stage 7 Tablets
0.036 mg. 17α-ethinylestradiol
0.50 mg. D-17β-acetoxy-13β-ethyl-17α-ethinyl-gon-4-en-3-one oxime
87.9 mg. lactose anhydrous DT
11.1 mg. pregalatanized starch N.F.
0.5 mg. magnesium stearate N.T.
100.036 mg. total weight 2nd Stage 7 Tablets
0.036 mg. 17α-ethinylestradiol
0.75 mg. D-17β-acetoxy-13β-ethyl-17α-ethinyl-gon-4-en-3-one oxime
89.70 mg. lactose anhydrous DT
9.02 mg. pregalatanized starch N.F.
0.5 mg. magnesium stearate N.T.
100.006 mg. total weight 3rd Stage 7 Tablets
0.036 mg. 17α-ethinylestradiol
1.0 mg. D-17β-acetoxy-13β-ethyl-17α-ethinyl-gon-4-en-3-one oxime
87.5 mg. lactose anhydrous DT
11.0 mg. pregalatanized starch N.F.
0.5 mg. magnesium stearate N.T.
100.036 mg. total weight

EXAMPLE 3

Composition of a tablet for each stage:

1st Stage 7 Tablets
0.035 mg. 17α-ethinylestradiol
0.50 mg. d-norgestrel
90.0 mg. lactose anhydrous DT
9.0 mg. pregalatanized starch N.F.
0.5 mg. magnesium stearate N.T.
100.035 mg. total weight 2nd Stage 7 Tablets
0.035 mg. 17α-ethinylestradiol
0.75 mg. d-norgestrel
87.70 mg. lactose anhydrous DT
11.02 mg. pregalatanized starch N.F.
0.5 mg. magnesium stearate N.T.
100.005 mg. total weight 3rd Stage 7 Tablets
0.035 mg. 17α-ethinylestradiol
1.0 mg. d-norgestrel
89.5 mg. lactose anhydrous DT
9.0 mg. pregalatanized starch N.F.
0.5 mg. magnesium stearate N.T.
100.035 mg. total weight

Clinical Tests

EXAMPLE 4

A preparation according to Example 1 was administered in three separate studies to a total of 656 women of child-bearing age. Subjects meeting the selection criteria were administered the contraceptive formulation on a regimen of 21 days on medication and 7 days off for up to 12 cycles.

The preparation was shown to be highly efficacious in preventing pregnancy. In each study the bleeding pattern consistently showed a decrease in the incidence of midcycle breakthrough bleeding and/or spotting.

Having described the invention in specific detail and exemplified the manner in which it may be carried into practice, it will be apparent to those skilled in the art that innumerable variations, applications, modifications, and extensions of the basic principles involved may be made without departing from its spirit or scope. It is to be understood that the foregoing is merely exemplary and the present invention is not to be limited to the specific form or arrangements of parts herein described and shown.

I claim:

1. A method of contraception which comprises administering for 21 successive days to a female of childbearing age a combination of an estrogen and a progestogen in a low but contraceptively effective daily dosage corresponding in estrogenic activity to 0.02–0.05 mg of 17α-ethinylestradiol and in progestogenic activity to 0.125–0.75 mg of norethindrone for 7 days; for the next 7 days an estrogen daily dosage equal to 0.02–0.05 mg of 17α-ethinylestradiol and in progestogenic activity to 0.50–1.0 mg of norethindrone; and for the next 7 days an estrogen daily dosage equal to 0.02–0.05 mg of 17α-ethinylestradiol and in progestogenic activity of 0.75–2.0 mg of norethindrone; followed by 7 days without estrogen and progestrogen administration, provided that the estrogen daiy dosage is the same for each 7 day period.

2. The method of claim 1 wherein the estrogen and progestogen are administered orally.

3. The method of claim 1 wherein the estrogen and progestogen are administered in admixture.

4. The method of claim 1 wherein the progestogen is selected from d-norgestrel, norethindrone, progesterone and D-17β-acetoxy-13β-ethyl-17α-ethinyl-gon-4-en-3-one oxime.

5. The method of claim 1 wherein the estrogen is selected from 17α-ethinylestradiol, estrone, estradiol and estriol.

6. The method of claim 1 wherein the estrogen is 17α-ethinylestradiol and the progestogen is norethindrone.

7. The method of claim 1 wherein the estrogen is 17α-ethinylestradiol and the progestogen is D-17β-acetoxy-13β-ethyl-17α-ethinyl-gon-4-en-3-one oxime.

8. The method of claim 1 wherein the estrogen daily dosage is 0.035 mg for each 7 day period and the progestogen daily dosage is 0.5 mg for the first 7 days, 0.75 mg for the second 7 days and 1.0 mg for the third 7 days.

9. The contraception method of claim 1 which comprises administering for 21 successive days to a female of childbearing age a combination of 17α-ethinylestradiol and norethindrone in a contraceptively effective daily dosage corresponding to 0.035 mg of 17α-ethinylestradiol and 0.50 mg of norethindrone for 7 days; for the next 7 days a daily dosage equal to 0.035 mg of 17α-ethinylestradiol and 0.75 mg of norethindrone; and for the next 7 days a daily dosge equal to 0.035 mg of 17α-ethinylestradiol and 1.0 mg of norethindrone; followed by 7 days without estrogen and progestogen administration.

* * * * *